United States Patent
Min et al.

(10) Patent No.: US 8,993,766 B2
(45) Date of Patent: Mar. 31, 2015

(54) METHOD OF PREPARING TETRABENAZINE AND DIHYDROTETRABENAZINE

(75) Inventors: Sun Joon Min, Seoul (KR); Yong Seo Cho, Seoul (KR); Jae Kyun Lee, Seoul (KR); Ae Nim Pae, Seoul (KR); Young Wook Son, Gyeonggi-do (KR)

(73) Assignee: Korea Institute of Science and Technology, Seoul (KR)

( * ) Notice: Subject to any disclaimer, the term of this patent is extended or adjusted under 35 U.S.C. 154(b) by 189 days.

(21) Appl. No.: 13/617,357

(22) Filed: Sep. 14, 2012

(65) Prior Publication Data

US 2013/0197227 A1 Aug. 1, 2013

(30) Foreign Application Priority Data

Jan. 31, 2012 (KR) .................. 10-2012-0009756

(51) Int. Cl.
*C07D 455/06* (2006.01)
*C07F 7/08* (2006.01)

(52) U.S. Cl.
CPC ............ *C07D 455/06* (2013.01); *C07F 7/0812* (2013.01)
USPC ............................................ 546/94

(58) Field of Classification Search
CPC .................................................. C07D 455/06
USPC ........................................................... 546/95
See application file for complete search history.

(56) References Cited

PUBLICATIONS

William G. Ondo et al., "Tetrabenazine Treatment for Tardive Dyskinesia: Assessment by Randomized Videotape Protocol", American Journal of Psychiatry 156:8, Aug. 1999, pp. 1279-1281.
Joseph Jankovic et al., "Long-term effects of tetrabenazine in hyperkinetic movement disorders", American Academy of Neurology, 1997.
Michael J. Rishel et al., "Asymmetric Synthesis of Tetrabenazine and Dihydrotetrabenazine", American Chemical Society, Apr. 17, 2009, pp. 4001-4004.
Seung-Mann Paek et al., "A Concise Total Synthesis of (+)-Tetrabenazine and (+)-α-Dihydrotetrabenazine", Chemistry European Journal, 2010, pp. 4623-4628.
Young Wook Son et al., "A Concise Synthesis of Tetrabenazine: An Intramolecular Aza=Prins-Type Cyclization via Oxidative C—H Activation", Organic Letter, 2011, vol. 13, No. 24, pp. 6500-6503.

*Primary Examiner* — David K O Dell
(74) *Attorney, Agent, or Firm* — Goldilocks ZONE IP LAW

(57) ABSTRACT

The present invention relates to a method for preparing tetrabenazine (TBZ) and dihydrotetrabenazine (DTBZ), and more specifically to a method for preparing tetrabenazine (TBZ) and dihydrotetrabenazine (DTBZ) by using simple and short reaction processes of using 6,7-dimethoxy-1,2,3,4-tetrahydroisoquinoline and 4-methyl-2-(3-(trimethylsilyl)prop-1-ene-2-yl)pentane as starting materials to sequentially perform an alkylation reaction, an Aza-Prins cyclization reaction in the presence of an oxidant and an oxidation reaction.

8 Claims, No Drawings

METHOD OF PREPARING TETRABENAZINE AND DIHYDROTETRABENAZINE

CROSS-REFERENCE TO RELATED APPLICATIONS

This application claims priority to and the benefit of Korean Patent Application No. 10-2012-0009756 filed in the Korean Intellectual Property Office on Jan. 31, 2012, the entire contents of which are incorporated herein by reference.

TECHNICAL FIELD

The present invention relates to a method for preparing tetrabenazine (TBZ) and dihydrotetrabenazine (DTBZ) which is a metabolite thereof.

BACKGROUND ART

Tetrabenazine (TBZ) has a chemical structure represented by the following Formula 1, and the chemical name thereof is 1,3,4,6,7,11b-hexahydro-9,10-dimethoxy-3-(2-methoxypropyl)-2H-benzo(a)quinolizin-2-one.

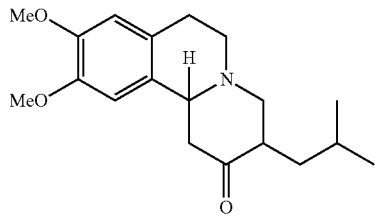

[Formula 1]

Further, dihydrotetrabenazine (DTBZ) is a metabolite of tetrabenazine (TBZ) and a product produced by reducing a 2-keto group of tetrabenazine, and has a chemical structure represented by the following Formula 2. The chemical name thereof is 2-hydroxy-3-(2-methoxypropyl)-1,3,4,6,7,11b-hexahydro-9,10-dimethoxy-benzo(a)quinolizine.

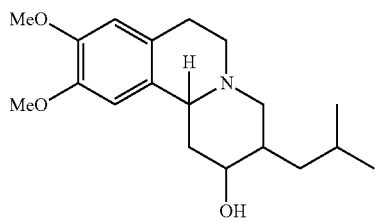

[Formula 2]

Tetrabenazine (TBZ) and dihydrotetrabenazine (DTBZ) are used as a therapeutic agent for neuropathy, mental disorder and the like by selectively binding to vesicular monoamine transporter-2 (VMAT2) [Jankovic et al., Am. J. Psychiatry. (1999) August; 156(8):1279-81 and Jankovic et al., Neurology (1997) February; 48(2):358-62]. Tetrabenazine (TBZ) was first synthesized in 1956, approved as a therapeutic medicine for neural diseases, mental diseases and the like in Finland, the Netherlands, Switzerland, England and the like, approved by the FDA in 2008, and has been currently used as a therapeutic agent for chorea symptoms of Huntington's disease. TBZ derivatives have been currently used as an imaging agent and a biomarker probe for diabetes and the like.

Representative methods for preparing tetrabenazine (TBZ), which have been recently know, are performed by using an addition reaction of non-symmetric malonate under a palladium catalyst [J. Org. Chem. 2009, 74, 4001]. That is, dihydroisoquinoline which is a starting material was introduced into malonate by using a palladium catalyst and (S)-DM-binap, and then was subjected to a reaction process including a total of 9 steps, such as Krapcho method and the like, to prepare a target compound.

As another preparation method of tetrabenazine (TBZ), dihydroisoquinoline which is a starting material was subjected to a reaction process including a total of 7 steps including a non-symmetric allylation reaction, a stereoselective enol-etherification reaction, an aza-Claisen rearrangement reaction and a transannulation reaction under an acid catalyst to prepare tetrabenazine [Chem-A. Eur. J. 2010, 16, 4623].

As studied above, tetrabenazine (TBZ) and dihydrotetrabenazine (DTBZ) which is a metabolite thereof are compounds which have high medical use values, and an industrial mass production thereof is required, but preparation methods released until now include multi-step processes and thus have limitations for commercial use.

SUMMARY OF THE INVENTION

The present invention has been made in an effort to provide a method for preparing tetrabenazine (TBZ) and dihydrotetrabenazine (DTBZ) by simple and short reaction processes by using 6,7-dimethoxy-1,2,3,4-tetrahydroisoquinoline and 4-methyl-2-(3-(trimethylsilyl)prop-1-ene-2-yl)pentane as starting materials.

An exemplary embodiment of the present invention provides a method for preparing tetrabenazine or dihydrotetrabenazine, including: a process of subjecting a compound represented by the following Formula 3 and a compound represented by the following Formula 4 to an alkylation reaction to prepare a compound represented by the following Formula 5, as shown in the following Reaction Scheme 1; a process of subjecting the compound represented by the following Formula 5 to an Aza-Prins cyclization reaction in the presence of an oxidant to prepare a ring compound represented by the following Formula 6; a process of subjecting the ring compound represented by the following Formula 6 to an oxidation reaction, such that a methylene group of the ring compound is converted into a keto group, to prepare tetrabenazine represented by the following Formula 1; and a process of subjecting the tetrabenazine represented by the following Formula 1 to a reduction reaction, such that a keto group of the tetrabenazine is converted into a hydroxyl group, to prepare dihydrotetrabenazine represented by the following Formula 2.

[Reaction Scheme 1]

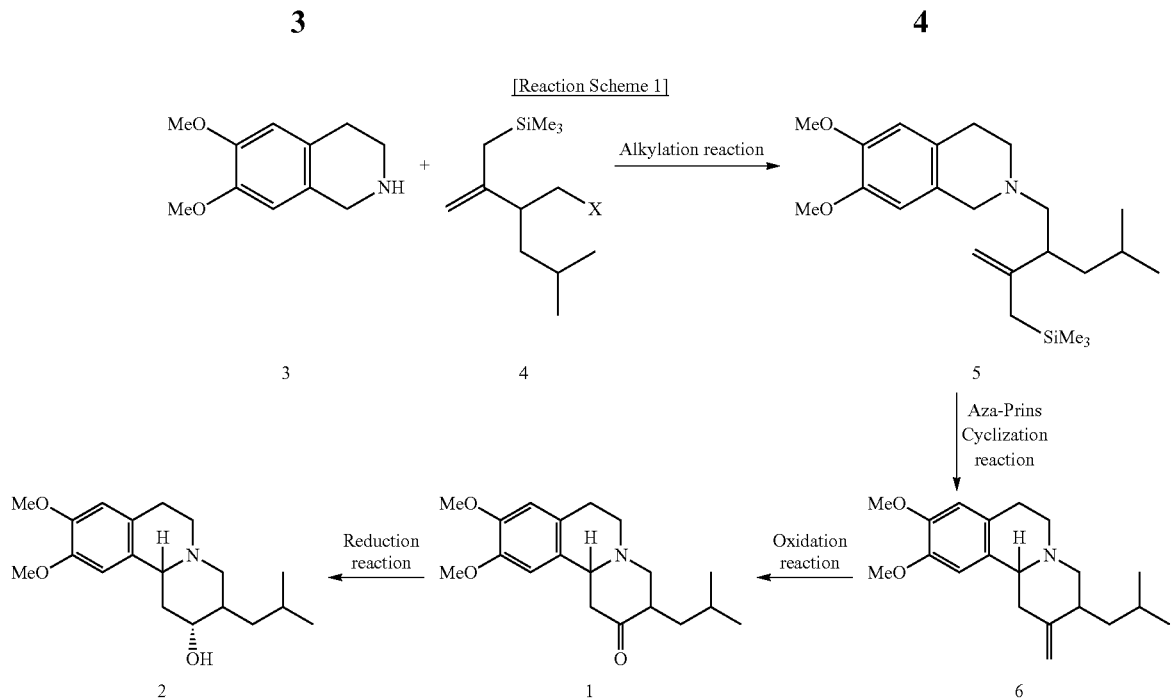

In Reaction Scheme 1, X is a leaving group and represents a halogen element, a methanesulfonyloxy group or a p-toluenesulfonyloxy group.

Another exemplary embodiment of the present invention provides a compound represented by Formula 5 and a compound represented by Formula 6 as a novel intermediate compound for synthesis of tetrabenazine or dihydrotetrabenazine.

The preparation method of the present invention has short and simple processes compared to the preparation method of tetrabenazine (TBZ) or dihydrotetrabenazine (DTBZ) in the related art, and thus is useful as a mass production method of tetrabenazine (TBZ) or dihydrotetrabenazine (DTBZ).

DETAILED DESCRIPTION

The present invention relates to a method for preparing tetrabenazine (TBZ) or dihydrotetrabenazine (DTBZ) by using simple and short reaction processes of using 6,7-dimethoxy-1,2,3,4-tetrahydroisoquinoline represented by Formula 3 and 4-methyl-2-(3-(trimethylsilyl)prop-1-ene-2-yl)pentane represented by Formula 4 as starting materials to sequentially perform an alkylation reaction, an Aza-Prins cyclization reaction in the presence of an oxidant and an oxidation reaction.

The preparation method according to the present invention will be described in more detail as follows.

A first process is a process of reacting the starting materials represented by Formulae 3 and Formula 4 to prepare the alkylated compound represented by Formula 5.

The alkylation reaction is performed by heating the compound in the presence of a base. At this time, the reaction is performed in the presence of a typical inorganic base including an alkali metal carbonate, a hydrogen carbonate, a sulfate, a hydrogen sulfate and the like as the base, and sodium carbonate or potassium carbonate is preferably used. The heating is performed by maintaining the temperature in a range of from 30° C. to the reflux temperature of the solvent, and specifically in a range of from 30° C. to 150° C. The organic solvent is a typical one used in the art, and dichloromethane, dimethylformamide (DMF), dimethylacetamide (DMAc), dioxane and the like may be used.

A second process is a process of subjecting the compound represented by Formula 5 to an Aza-Prins cyclization reaction in the presence of an oxidant to prepare the ring compound represented by Formula 6.

The Aza-Prins cyclization reaction is performed by heating the compound in the presence of an oxidant, a molecular sieve and $LiClO_4$. The oxidant is selected from phenyliodine diacetate (PIDA), phenyliodine bis(trifluoroacetate)diacetate (PIFA) and dichlorodicyanoquinone (DDQ) and used, and dichlorodicyanoquinone (DDQ) is preferably used. The above-described oxidant is used in an amount of from 1.0 equivalent to 3.0 equivalents and preferably from 1.3 equivalents to 1.5 equivalents, relative to the compound represented by Formula 5. The molecular sieve has a particle diameter of from 3 Å to 10 Å and preferably from 3 Å to 5 Å, and is used at a mass ratio of from 2 to 10 relative to the compound represented by Formula 5. The $LiClO_4$ is used in an amount of from 0.1 to 1.0 equivalent and preferably from 0.3 to 0.5 equivalent relative to the compound represented by Formula 5. The Aza-Prins cyclization reaction temperature is from normal temperature to the reflux temperature of the solvent, and maintained at specifically from 20° C. to 150° C. and preferably at a temperature in the vicinity of normal temperature, for example, from 20° C. to 30° C. The reaction solvent is an organic solvent typically used in the art, and acetonitrile ($CH_3CN$), dichloromethane ($CH_2Cl_2$), trichloromethane ($CHCl_3$), dimethylformamide (DMF), tetrahydrofuran (THF) and the like may be used. In performing the Aza-Prins cyclization reaction of the present invention, the reaction is particularly preferably performed at normal temperature by using a DDQ oxidant/$LiClO_4$/dichloromethane($CH_2Cl_2$).

A third process is a process of subjecting the ring compound represented by Formula 6 to an oxidation reaction to prepare the tetrabenazine represented by Formula 1.

That is, in the third process, a methylene group at the C-2 position of the ring compound represented by Formula 6 is oxidized to be converted into a keto group. The oxidation reaction is performed in the presence of $OsO_4$, $NaIO_4$ and N-methylmorpholine-N-oxide (NMO). The oxidation reaction temperature is maintained at from −20° C. to 30° C. and preferably from −10° C. to 10° C. The reaction solvent is an organic solvent typically used in the art, and acetonitrile ($CH_3CN$), dichloromethane ($CH_2Cl_2$), trichloromethane ($CHCl_3$), dimethylformamide (DMF), tetrahydrofuran (THF) and the like may be used.

A fourth process is a process of subjecting the tetrabenazine represented by Formula 1 to a reduction reaction to prepare the dihydrotetrabenazine represented by Formula 2.

That is, in the fourth process, the keto group of the tetrabenazine represented by Formula 1 is converted into a hydroxyl group. In the reduction reaction, $NaBH(OAc)_3$, $NaBH_3CN$, $NaBH_4$ and the like may be used as a reductant, and the amount of the reductant used is slightly different depending on the reactivity thereof and is from 2 equivalents to 10 equivalents and preferably from 2 equivalents to 3 equivalents. The reduction reaction temperature is maintained at from −20° C. to 30° C. and preferably from −10° C. to 10° C. The reaction solvent is an organic solvent typically used in the art, and methanol, ethanol, acetonitrile ($CH_3CN$), dichloromethane ($CH_2Cl_2$), trichloromethane ($CHCl_3$), dimethylformamide (DMF), tetrahydrofuran (THF) and the like may be used.

The above-described preparation method of the present invention may obtain an effect of greatly reducing processes, compared to the preparation method in the related art by taking a synthetic route of the compound represented by Formula 5 and the compound represented by Formula 6 as reaction intermediates. Therefore, the present invention includes, as a scope thereof, the compound represented by Formula 5 and the compound represented by Formula 6, which are useful as an intermediate compound for preparation of tetrabenazine or dihydrotetrabenazine.

The present invention as described above will be described in more detail with reference to the following Examples, but the present invention is not limited thereto.

EXAMPLE

Example 1

6,7-dimethoxy-2-(4-methyl-2(3-(trimethylsilyl)prop-1-ene-2-yl)pentyl)-1,2,3,4-tetrahydroisoquinoline (Compound of Formula 5)

(3-(tosylmethyl)-5-methyl-2-methylenehexyl)trimethylsilane (Formula 4; 72.0 mg, 0.195 mmol) and $Na_2CO_3$ (41.4 mg, 0.391 mmol) were added to DMF (2 mL). Then, 6,7-dimethoxy-1,2,3,4-tetrahydroisoquinoline (Formula 3; 75.4 mg, 0.391 mmol) was added thereto, and the mixture was heated up to 80° C. and stirred for 30 hr. Distilled water was put into the reaction solution to complete the reaction, and then the temperature was increased to normal temperature. An organic layer was extracted, the organic layer collected was washed with distilled water and a brine solution, and the remaining solvent was distilled under reduced pressure. Anhydrous magnesium sulfate was used to dry the organic layer, filtration under reduced pressure and evaporation under reduced pressure were performed, and then column chromatography was used to obtain 53.3 mg (yield 75%) of the title compound.

$^1$H NMR (400 MHz, $CDCl_3$) d 0.59 (s, 9H), 0.87 (d, J=5.6 Hz, 3H), 0.89 (d, J=5.6 Hz, 3H), 1.24-1.34 (m, 2H), 1.37-1.43 (ddd, J=9.2, 8.8, 3.6 Hz, 1H), 1.51 (d, J=4 Hz, 2H), 1.59-1.70 (m, 1H), 2.31-2.35 (m, 1H), 2.37 (dd, J=7.2, 7.6 Hz, 1H), 2.42-2.47 (m, 1H), 2.57-2.63 (m, 1H), 2.70-2.75 (dd, J=6.5, 7.0 Hz, 1H), 2.76-2.80 (m, 2H), 3.52 (s, 2H), 3.86 (s, 6H), 4.68 (s, 1H), 4.71 (s, 1H), 6.53 (s, 3H), 6.56 (s, 3H); $^{13}$C NMR (100 MHz, $CDCl_3$) d 0.00, 23.06, 24.46, 25.05, 26.13, 29.51, 42.36, 43.46, 51.79, 56.71, 57.04, 63.78, 109.05, 110.27, 112.16, 127.31, 127.91, 147.91, 148.15, 150.46;

Example 2

3-isobutyl-9,10-dimethoxy-2-methylen-2,3,4,6,7,11b-hexahydro-1H-pyrido[2,1-a]isoquinoline (Compound of Formula 6)

6,7-dimethoxy-2-(4-methyl-2(3-(trimethylsilyl)prop-1-ene-2-yl)pentyl)-1,2,3,4-tetrahydroisoquinoline (Formula 5; 18.4 mg, 0.0693 mmol) and a 4 Å molecular sieve (100 mg) were put into anhydrous $CH_2Cl_2$ (0.5 mL) and stirred. A solution obtained by dissolving 2,3-dichloro-5,6-dicyano-1,4-benzoquinone (DDQ; 19.3 mg, 0.104 mmol) and $LiClO_4$ (2.19 mg, 0.0208 mmol) in anhydrous $CH_2Cl_2$ (0.5 mL) in a separate container was slowly added to the reaction solution and stirred for 20 min. A saturated $NaHCO_3$ aqueous solution (1 mL) was added thereto to complete the reaction. An organic layer was extracted, and then the organic layer collected was washed with distilled water and a brine solution. Anhydrous magnesium sulfate was used to dry the organic layer, filtration under reduced pressure and evaporation under reduced pressure were performed, and then column chromatography was used to obtain 8.22 mg (yield 55%) of the title compound.

$^1$H NMR (400 MHz, $CDCl_3$) d 0.91 (d, J=6.5 Hz, 3H), 0.93 (d, J=6.5 Hz, 3H), 1.18-1.25 (m, 1H), 1.45-1.49 (m, 1H), 1.68-1.76 (m, 2H), 1.97 (dd, J=11.1, 11.1 Hz, 1H), 2.21 (m, 1H), 2.41 (m, 1H), 2.45-2.53 (ddd, J=3.9, 11.1, 11.2 Hz, 1H), 2.63-2.67 (dd, J=2.3, 16.2 Hz, 1H), 2.80-2.84 (dd, J=2.7, 12.9 Hz, 1H), 2.99-3.02 (ddd, J=1.89, 5.3, 5.7 Hz, 1H), 3.04-3.15 (m, 3H), 3.85 (s, 3H), 3.87 (s, 3H), 4.74 (d, J=1.1 Hz, 1H), 4.90 (d, J=1.3 Hz, 1H), 6.59 (d, J=3.4 Hz, 1H), 6.69 (s, 1H); $^{13}$C NMR (100 MHz, $CDCl_3$) d 22.19, 23.83, 25.05, 29.21, 38.67, 38.87, 41.90, 51.80, 55.85, 56.07, 62.96, 64.13, 106.18, 108.19, 111.48, 126.63, 129.77, 147.18, 147.52, 150.23.

Example 3

1,3,4,6,7,11b-hexahydro-9,10-dimethoxy-3-(2-methoxypropyl)-2H-benzo(a)quinolizin-2-one (Compound of Formula 1)

3-isobutyl-9,10-dimethoxy-2-methylen-2,3,4,6,7,11b-hexahydro-1H-pyrido[2,1-a]isoquinoline (Formula 6); 11.3 mg, 0.0358 mmol) was dissolved in a mixed solvent of THF (3 mL) and $H_2O$ (1 mL), the mixture was cooled to 0° C., then $OsO_4$ (4 weight % aqueous solution, 0.711 mL, 0.0125 mmol) was added thereto, and the resulting mixture was stirred at 0° C. for 15 min. $NaIO_4$ (38.3 mg, 0.179 mmol) dissolved in $H_2O$ (1 mL) and N-methylmorpholine-N-oxide (NMO; 20.9 mg, 0.179 mmol) dissolved in $H_2O$ (1 mL) were added to the reaction solution, the resulting mixture was further stirred at 0° C. for 5 hr, and then a saturated $Na_2SO_3$ aqueous solution was added thereto to complete the reaction. Ethyl acetate and water were added thereto to extract an organic layer, and the organic layer collected was washed with a brine solution. Anhydrous magnesium sulfate was used to dry the organic layer, filtration under reduced pressure and evaporation under reduced pressure were performed, and then column chromatography was used to obtain 6.78 mg (yield 61%) of the title compound.

$^1$H NMR (400 MHz, CDCl$_3$) d 0.89 (d, J=6.4 Hz, 3H), 0.92 (d, J=6.5 Hz, 3H), 0.99-1.06 (m, 1H), 1.58-1.68 (m, 1H), 1.76-1.82 (m, 1H), 2.34 (dd, J=11.6, 13.2 Hz, 1H), 2.50-2.61 (m, 2H), 2.70-2.74 (m, 2H), 2.89 (dd, J=2.7, 13.6 Hz, 1H), 3.11 (m, 2H), 3.28 (dd, J=6.1, 11.5 Hz, 1H), 3.50 (d, J=10.5 Hz, 1H), 3.82 (s, 3H), 3.84 (s, 3H), 6.53 (s, 1H), 6.60 (s, 1H); $^{13}$C NMR (100 MHz, CD$_3$OD) d 21.11, 22.08, 25.20, 28.51, 34.87, 46.14, 46.37, 49.72, 54.94, 55.18, 60.66, 62.20, 108.38, 111.56, 125.97, 128.40, 147.58, 148.07.

Example 4

2-hydroxy-3-(2-methoxypropyl)-1,3,4,6,7,11b-hexahydro-9,10-dimethoxy-benzo(a)quinolizine (Compound of Formula 2)

Tetrabenazine (Formula 1; 9.01 mg, 0.0284 mmol) was dissolved in 1 mL of ethanol, the solution was cooled to 0° C., and then NaBH$_4$ (3.22 mg, 0.0851 mmol) was slowly added thereto. The temperature was heated to normal temperature and then the mixture was stirred for 1 hr. The mixture was distilled under reduced pressure, water (3 mL) and CH$_2$Cl$_2$ (3 mL) were added thereto to extract an organic layer, and the organic layer collected was washed with a saturated K$_2$CO$_3$ aqueous solution. Anhydrous magnesium sulfate was used to dry the organic layer, filtration under reduced pressure and evaporation under reduced pressure were performed, and then column chromatography was used to obtain 7.30 mg (yield 80%) of the title compound.

$^1$H NMR (400 MHz, CDCl$_3$) d 0.91 (d, J=6.8 Hz, 3H), 0.93 (d, J=7.6 Hz, 3H), 1.06 (ddd, J=4.0, 11.6, 12.0 Hz, 1H), 1.57-1.63 (m, 2H), 1.64-1.70 (m, 2H), 1.83 (m, 1H), 2.06 (t, J=10.8, 11.6 Hz, 1H), 2.51-2.56 (m, 1H), 2.59-2.62 (m, 1H), 2.68 (d, J=15.2, 1H), 3.09-3.17 (m, 2H), 3.23-3.26 (m, 1H), 3.42 (dt, J=4.4, 10.0, 10.4, 1H), 3.84 (s, 6H), 6.58 (s, 1H), 6.66 (s, 1H); $^{13}$C NMR (75 MHz, CDCl$_3$) d 21.76, 24.15, 25.36, 28.60, 29.72, 39.62, 40.23, 41.22, 51.68, 55.87, 55.97, 59.83, 60.93, 74.30, 107.88, 111.44, 126.03, 128.70, 147.36, 147.69

PREPARATIVE EXAMPLE

Synthesis of Intermediate Compound

Preparative Example 1

Preparation of methyl 2-(hydroxymethyl)-4-methyl pentanoate

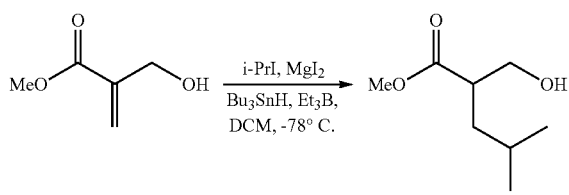

MgI$_2$ (683 mg, 2.45 mmol) was added to anhydrous CH$_2$Cl$_2$ (6 mL), and the mixture was stirred at normal temperature for 45 min. The mixture was cooled to −78° C., and then methyl 2-(hydroxymethyl)acrylate dissolved in anhydrous CH$_2$Cl$_2$ (8 mL) was added thereto. The mixture was further stirred at −78° C. for 30 min, and then isopropyl iodide (417 mg, 24.5 mmol), Bu$_3$SnH (2.57 mg, 8.84 mmol) and Et$_3$B (8.84 mL, 8.84 mmol, 1.0 M/hexane solution) in sequence were slowly added thereto. Immediately after all were added thereto, air (20 mL) was slowly added thereto through a syringe. After the mixture was stirred for 2 hr and 30 min, the reactant was diluted in diethyl ether (120 mL). Silica gel (10 g) was added thereto, and then the resulting mixture was evaporated under reduced pressure. The powder obtained was washed with hexane (500 mL) and extracted with diethyl ether (300 mL), evaporation was performed under reduced pressure, and then column chromatography was used to obtain 150 mg (yield 78%) of the title compound.

$^1$H NMR (300 MHz, CDCl$_3$) d 0.87 (d, J=6.0 Hz, 3H), 0.88 (d, J=5.4 Hz, 3H), 1.32-1.38 (m, 1H), 1.41-1.76 (m, 2H), 2.34 (s, 1H), 2.45-2.86 (m, 1H), 3.68-3.70 (m, 2H), 3.68 (s, 3H); $^{13}$C NMR (75 MHz, CDCl$_3$) d 22.16, 22.43, 25.78, 37.86, 45.45, 51.89, 63.38, 162.18, 176.11.

Preparative Example 2

Preparation of methyl 4-methyl-2-(((tetrahydro-2H-pyran-2-yl)oxy)methyl)pentanoate

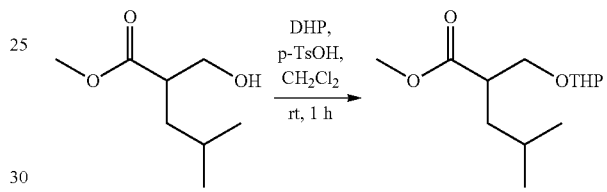

Methyl 2-(hydroxymethyl)-4-methyl pentanoate (483 mg, 3.01 mmol) and 3,4-dihydro-2H-pyrane (304 mg, 3.62 mmol) were dissolved in CH$_2$Cl$_2$ (12 mL), and then p-toluene sulfonic acid (57.3 mg, 0.301 mmol) was added thereto. The reactant was stirred at normal temperature for 1 hr, and then a saturated NaHCO$_3$ aqueous solution (10 mL) was added thereto. Extraction was performed by using ethyl acetate, anhydrous magnesium sulfate was used to perform drying and distillation under reduced pressure, and then column chromatography was used to obtain 650 mg (yield 921%) of the title compound.

$^1$H NMR (400 MHz, CDCl$_3$) d 0.87 (d, J=6.3 Hz, 3H), 0.89 (d, J=6.3 Hz, 3H), 1.23-1.3 (m, 1H), 1.44-1.57 (m, 6H), 1.58-1.60 (m, 1H), 1.60-1.80 (m, 1H), 2.73-2.81 (m, 1H), 3.39-3.56 (m, 2H), 3.67 (s, 1H), 3.68 (s, 1H'), 3.72-3.89 (m, 2H), 4.54 (t, J=3.2, 3.2 Hz, 1H), 4.61 (t, J=3.4, 3.5 Hz, 1H'); $^{13}$C NMR (100 MHz, CDCl$_3$) d 18.93, 19.39, 22.12, 22.88, 25.41, 26.10, 30.36, 30.51, 38.00, 38.06, 44.03, 44.40, 51.50, 61.54, 35.24, 68.24, 69.08, 97.81, 99.30, 175.38, 175.57.

Preparative Example 3

Preparation of N-methoxy-N,4-dimethyl-2-(((tetrahydro-2H-pyran-2-yl)oxy)methyl)pentane amide

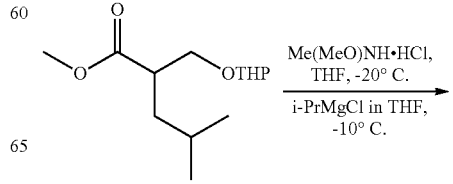

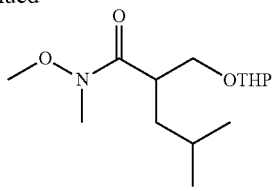

Methyl 4-methyl-2-((((tetrahydro-2H-pyran-2-yl)oxy)methyl)pentanoate (251 mg, 1.08 mmol) and Me(MeO)NH.HCl (157 mg, 1.61 mmol) were added to anhydrous THF (3 mL) and the mixture was cooled to −20° C. under nitrogen charge. An i-PrMgCl solution (1.62 mL, 2.0 M) dissolved in THF was slowly added thereto over 15 min by using a syringe. The mixture was further stirred at −10° C. for 20 min, and then a saturated NH$_4$Cl aqueous solution (2 mL) was added thereto to complete the reaction. Extraction was performed by using ethyl acetate, anhydrous magnesium sulfate was used to perform drying and distillation under reduced pressure, and then column chromatography was used to obtain 270 mg (yield 93%) of the title compound.

$^1$H NMR (400 MHz, CDCl$_3$) d 0.86 (d, J=7.8 Hz, 3H), 0.87 (d, J=7.8 Hz, 3H), 0.88 (d, J=7.0 Hz, 3H'), 0.89 (d, J=7.0 Hz, 3H'), 1.14-1.24 (m, 1H), 1.44-1.54 (m, 6H), 1.55-1.70 (m, 1H), 1.70-1.75 (m, 1H), 3.31 (s, 3H), 3.29-3.32 (m, 1H), 3.31-3.58 (m, 2H), 3.72 (s, 1H), 3.73 (s, 1H'), 3.71-3.90 (m, 2H), 4.50 (t, J=3.2, 3.2 Hz, 1H), 4.61 (t, J=3.5, 3.5 Hz, 1H'); $^{13}$C NMR (100 MHz, CDCl$_3$) d 18.97, 19.80, 22.44, 22.99, 25.39, 26.12, 30.36, 30.59, 32.09, 38.38, 38.46, 38.96, 39.22, 61.38, 62.62, 68.84, 69.74, 97.87, 99.54.

Preparative Example 4

Preparation of 5-methyl-3-((((tetrahydro-2H-pyran-2-yl)oxy)methyl)hexin-2-one

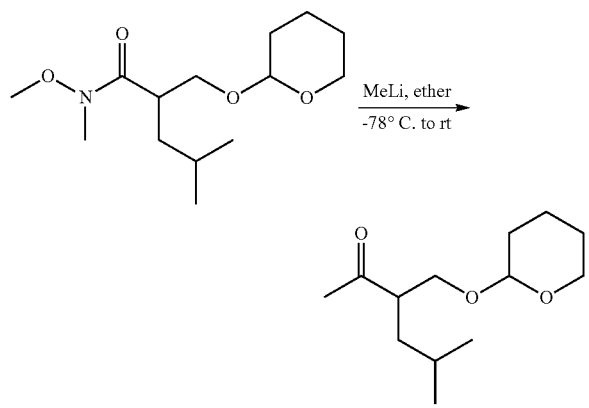

N-methoxy-N,4-dimethyl-2-((((tetrahydro-2H-pyran-2-yl)oxy)methyl)pentane amide (279 mg, 1.00 mmol) was dissolved in anhydrous Et$_2$O (5 mL), and then the solution was cooled to −78° C. MeLi (0.755 mL, 1.02 mmol, 1.6 M/hexane solution) was slowly added thereto under nitrogen charge by using a syringe. After the addition was all completed, the solution was slowly heated to normal temperature over 2 hr. After the solution was heated up to normal temperature, a saturated NH$_4$Cl aqueous solution (50 mL) was added to the reactant to complete the reaction. Extraction was performed by using ethyl acetate (3×10 mL), an organic layer was washed with distilled water (20 mL) and a brine solution (20 mL), anhydrous magnesium sulfate was used to perform drying and distillation under reduced pressure, and then column chromatography was used to obtain 210 mg (yield 92%) of the title compound.

$^1$H NMR (400 MHz, CDCl$_3$) d 0.87 (d, J=6.6 Hz, 3H), 0.88 (d, J=6.6 Hz, 3H), 1.14-1.24 (m, 1H), 1.44-1.56 (m, 6H), 1.58-1.60 (m, 1H), 1.60-1.81 (m, 1H), 2.18 (s, 3H), 2.20 (s, 3H'), 2.86-2.94 (m, 1H), 3.38-3.52 (m, 2H), 3.67-3.85 (m, 2H), 4.50 (t, J=3.8 Hz, 1H), 4.58 (t, J=3.1 Hz, 1H'); $^{13}$C NMR (100 MHz, CDCl$_3$) d 19.07, 19.52, 22.48, 22.86, 25.38, 36.03, 30.02, 30.42, 30.50, 37.50, 37.55, 50.71, 50.76, 61.72, 62.46, 68.58, 69.29, 98.18, 99.42, 211.68, 211.98.

Preparative Example 5

Preparation of 5-methyl-3-((((tetrahydro-2H-pyran-2-yl)oxy)methyl)hex-1-ene-2-yl tri fluoromethanesulfonate

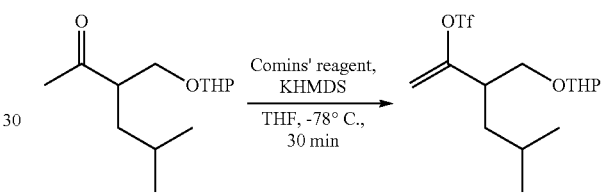

Potassium hexamethyldisilazide (KHMDS; 2.75 mL, 1.38 mmol, 0.5 M/toluene solution) was dissolved in THF (3 mL), and then the solution was cooled to −78° C. A solution obtained by dissolving 5-methyl-3-((((tetrahydro-2H-pyran-2-yl)oxy)methyl)hexin-2-one (210 mg, 0.920 mmol) in THF (3 mL) was slowly added to the reaction solution at −78° C. and the resulting solution was stirred for 30 min. A solution obtained by dissolving (N,N-bis(trifluoromethylsulfonyl)amino)-5-chloropyridine (541 mg, 1.38 mmol) in THF (3 mL) was slowly added to the reaction solution and the resulting solution was stirred for 40 min. A saturated NaHCO$_3$ aqueous solution (20 mL) was added thereto to complete the reaction, and then the solution was heated to normal temperature. Extraction was performed by using ethyl acetate (3×10 mL), an organic layer was washed with distilled water (30 mL) and a brine solution (30 mL), anhydrous magnesium sulfate was used to perform drying and distillation under reduced pressure, and then column chromatography was used to obtain 305 mg (yield 92%) of the title compound which is colorless and in the oil state.

$^1$H NMR (400 MHz, CDCl$_3$) d 0.85 (d, J=8.5 Hz, 3H), 0.85 (d, J=8.5 Hz, 3H'), 0.91 (d, J=8.5, 3H), 0.91 (d, J=8.5, 3H'), 1.10-1.39 (m, 1H), 1.44-1.80 (m, 6H), 1.62-1.80 (m, 2H), 2.58-2.68 (m, 1H), 3.32-3.39 (m, 1H), 3.46-3.50 (m, 1H), 3.69-3.83 (m, 2H), 4.53 (t, J=5.5 Hz, 1H), 4.58 (t, J=4.2 Hz, 1H'), 5.00 (dd, J=1.0, 3.8 Hz, 1H), 5.18 (dd, J=2.1, 3.8 Hz, 1H); $^{13}$C NMR (100 MHz, CDCl$_3$) d 19.09, 19.51, 22.04, 22.13, 22.89, 22.95, 25.10, 25.45, 30.39, 30.44, 37.86, 38.03, 42.61, 42.97, 61.85, 62.46, 67.52, 67.86, 98.46, 99.36, 104.14, 104.32, 157.36, 162.34

Preparative Example 6

Preparation of 3-(hydroxymethyl)-5-methylhex-1-ene-2-yl trifuloromethanesulfonate

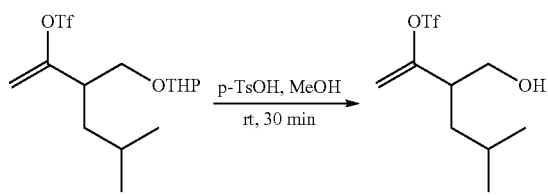

5-methyl-3-(((tetrahydro-2H-pyran-2-yl)oxy)methyl)hex-1-ene-2-yl trifluoromethanesulfonate (540 mg, 2.02 mmol) was dissolved in methanol (20 mL), and then p-toluene sulfonic acid (38.4 mg, 0.202 mmol) was added thereto. The resulting solution was stirred at normal temperature for 30 min and distilled under reduced pressure and then column chromatography was used to obtain 331 mg (yield 80%) of the title compound.

$^1$H NMR (400 MHz, CDCl$_3$) d 0.91 (d, J=6.3 Hz, 3H), 0.93 (d, J=6.3 Hz, 3H), 1.22-1.41 (m, 2H), 1.58 (s, 1H), 1.62-1.72 (m, 2H), 2.57-2.64 (m, 1H), 3.63 (dd, J=5.5 Hz, 2H), 3.32-3.39 (m, 1H), 3.46-3.50 (m, 1H), 3.69-3.83 (m, 2H), 4.53 (t, J=5.5 Hz, 1H), 5.08 (d, J=3.8 Hz, 2H), 5.27 (d, J=3.8 Hz, 2H); $^{13}$C NMR (100 MHz, CDCl$_3$) d 21.98, 22.95, 25.14, 36.99, 45.45, 62.67, 106.15, 156.27.

Preparative Example 7

Preparation of 4-methyl-2-(3-(trimethylsilyl)prop-1-ene-2-yl)pentan-1-ol

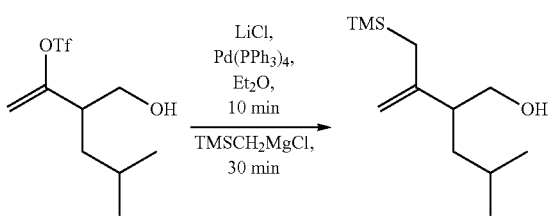 [SMILES: C=C(OS(=O)(=O)C(F)(F)F)C(CO)CC(C)C ; C=C(C[Si](C)(C)C)C(CO)CC(C)C]

LiCl (7.00 mg, 0.159 mmol) and Pd(PPh$_3$)$_4$ (2.30 mg, 0.002 mmol) were added to anhydrous Et$_2$O (1 mL), and then the resulting solution was cooled to 0° C. A solution obtained by dissolving 3-(hydroxymethyl)-5-methylhex-1-ene-2-yl trifluoromethanesulfonate (11 mg, 0.0398 mmol) in anhydrous Et$_2$O (1 mL) was slowly added thereto and the resulting solution was stirred for 10 min. TMSCH$_2$MgCl (0.119 mL, 0.119 mmol, 1.0 M/Et$_2$O solution) was slowly added thereto, the resulting solution was stirred for 1 hr, and then a saturated NH$_4$Cl aqueous solution (1 mL) was added thereto to complete the reaction. The temperature was increased to normal temperature, extraction was performed by using ethyl acetate (3×3 mL), distillation was performed under reduced pressure, and then column chromatography was used to obtain 8.03 mg (yield 94%) of the title compound.

$^1$H NMR (400 MHz, CDCl$_3$) δ 0.42 (s, 9H), δ 0.87 (d, J=6.5 Hz, 3H), 0.89 (d, J=6.6 Hz, 3H), 1.23-1.29 (m, 2H), 1.50 (dd, J=14.7, 14.8 Hz, 2H), 1.54-1.61 (m, 2H), 3.49-3.52 (m, 2H), 4.72 (s, 1H), 4.74 (d, J=2.0 Hz, 1H); $^{13}$C NMR (100 MHz, CDCl$_3$) δ 0.00, 23.80, 24.12, 26.24, 26.43, 40.46, 48.18, 64.46, 110.23, 149.20.

Preparative Example 8

Preparation of 4-methyl-2-(3-(trimethylsilyl)prop-1-ene-2-yl)pentyl 4-methylbenzenesulfonate

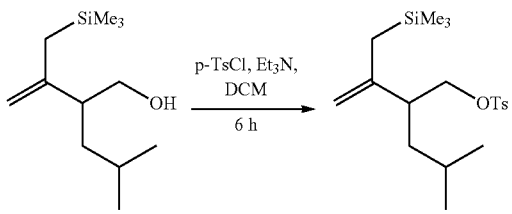 [SMILES: C=C(C[Si](C)(C)C)C(CO)CC(C)C ; C=C(C[Si](C)(C)C)C(COS(=O)(=O)c1ccc(C)cc1)CC(C)C]

4-methyl-2-(3-(trimethylsilyl)prop-1-ene-2-yl)pentan-1-ol (59.1 mg, 0.275 mmol) and triethyl amine (835 mg, 8.25 mmol) were dissolved in anhydrous CH$_2$Cl$_2$ (20 mL), and then the solution was cooled to 0° C. p-toluenesulfonyl chloride (57.7 mg, 0.303 mmol) and DMAP (2.00 mg, 0.0138 mmol) were added thereto and the resulting solution was stirred at 0° C. for 6 hr. Water (30 mL) was added thereto to complete the reaction, extraction was performed by using CH$_2$Cl$_2$ (3×20 mL), an organic layer was washed with a brine solution, anhydrous magnesium sulfate was used to perform drying and distillation under reduced pressure, and then column chromatography was used to obtain 75.1 mg (yield 74%) of the title compound which is colorless and in the oil state.

$^1$H NMR (400 MHz, CDCl$_3$) d –0.02 (s, 9H), 0.82 (d, J=6.6 Hz, 3H), 0.83 (d, J=6.5 Hz, 3H), 1.52-1.75 (m, 3H), 1.62-1.72 (m, 2H), 1.80-1.86 (m, 1H), 2.50-2.58 (m, 1H), 2.44 (s, 3H), 4.15-4.28 (m, 1H), 4.58 (s, 1H), 4.64 (d, J=1.0 Hz, 1H), 7.33 (d, J=8.0 Hz, 2H), 7.77 (d, J=6.7 Hz, 2H); $^{13}$C NMR (100 MHz, CDCl$_3$) d 0.00, 22.79, 23.76, 24.08, 26.32, 26.69, 41.22, 44.85, 75.66, 110.64, 129.14, 130.92, 134.34, 145.78, 147.15.

The preparation method of the present invention is useful for a mass production of tetrabenazine (TBZ) and dihydrotetrabenazine (DTBZ), which have been used as a therapeutic agent for neuropathy, mental disorder and the like and particularly, as a therapeutic agent for chorea symptoms of Huntington's disease.

What is claimed is:

1. A method for preparing tetrabenazine, comprising:
   a process of subjecting a compound represented by the following Formula 3 and a compound represented by the following Formula 4 to an alkylation reaction to prepare a compound represented by the following Formula 5;
   a process of subjecting the compound represented by the following Formula 5 to an Aza-Prins cyclization reaction in the presence of an oxidant to prepare a ring compound represented by the following Formula 6; and
   a process of subjecting the ring compound represented by the following Formula 6 to an oxidation reaction, such that a methylene group of the ring compound is converted into a keto group, to prepare tetrabenazine represented by the following Formula 1:

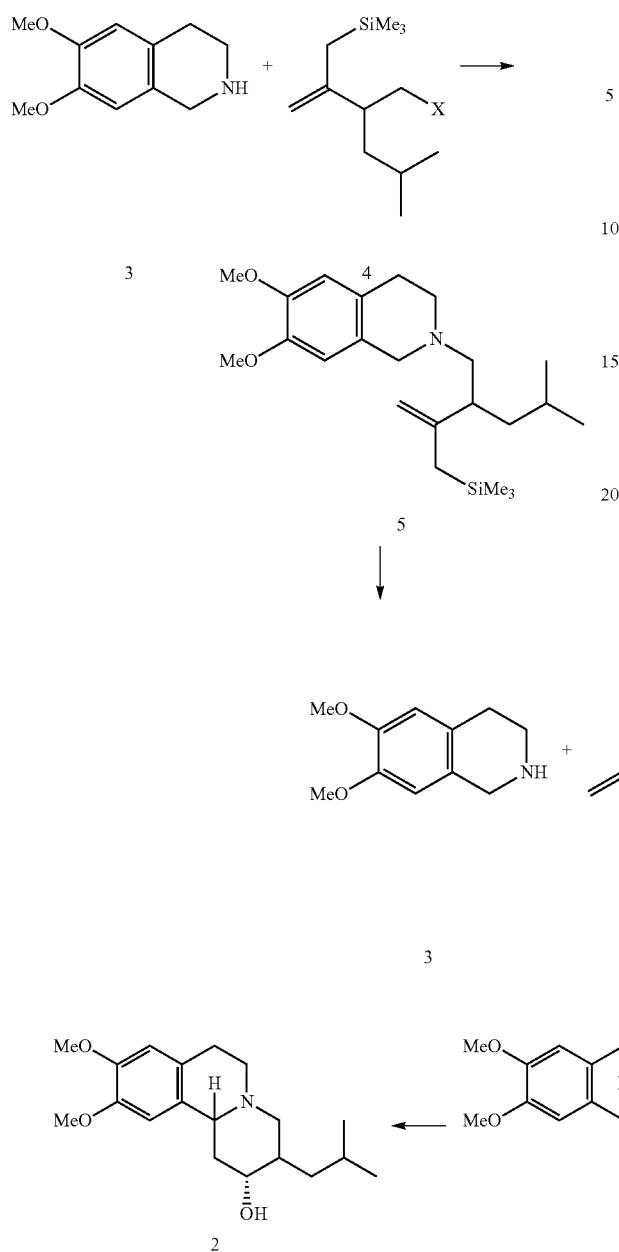

2. A method for preparing dihydrotetrabenazine, comprising:

a process of subjecting a compound represented by the following Formula 3 and a compound represented by the following Formula 4 to an alkylation reaction to prepare a compound represented by the following Formula 5;

a process of subjecting the compound represented by the following Formula 5 to an Aza-Prins cyclization reaction in the presence of an oxidant to prepare a ring compound represented by the following Formula 6;

a process of subjecting the ring compound represented by the following Formula 6 to an oxidation reaction, such that a methylene group of the ring compound is converted into a keto group, to prepare tetrabenazine represented by the following Formula 1; and a process of subjecting the tetrabenazine represented by the following Formula 1 to a reduction reaction, such that a keto group of the tetrabenazine is converted into a hydroxyl group, to prepare dihydrotetrabenazine represented by the following Formula 2:

in the Reaction Scheme, X is a leaving group and represents a halogen element, a methanesulfonyloxy group or a p-toluenesulfonyloxy group.

3. The method of claim 1, wherein the Aza-Prins cyclization reaction is performed in the presence of an oxidant selected from phenyliodine diacetate (PIDA), phenyliodine bis(trifluoroacetate)diacetate (PIFA) and dichlorodicyanoquinone (DDQ), a molecular sieve and LiClO₄.

4. The method of claim 3, wherein the Aza-Prins cyclization reaction is performed in the presence of an oxidant of dichlorodicyanoquinone and LiClO₄.

5. The method of claim 3, wherein the Aza-Prins cyclization reaction is performed at a temperature condition of from 20° C. to 150° C. in the presence of a solvent selected from acetonitrile (CH₃CN), dichloromethane (CH₂Cl₂), trichloromethane (CHCl₃), N,N-dimethylformamide (DMF) and tetrahydrofuran (THF).

6. 6,7-dimethoxy-2-(4-methyl-2(3-(trimethylsilyl)prop-1-ene-2-yl)pentyl)-1,2,3,4-tetrahydroisoquinoline represented by the following Formula 5, which is used as an intermediate compound for preparation of tetrabenazine or dihydrotetrabenazine.

[Formula 5]

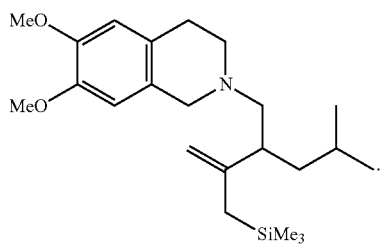

7. 3-isobutyl-9,10-dimethoxy-2-methylen-2,3,4,6,7,11b-hexahydro-1H-pyrido[2,1-a]isoquinoline represented by the following Formula 6, which is used as an intermediate compound for preparation of tetrabenazine or dihydrotetrabenazine.

[Formula 6]

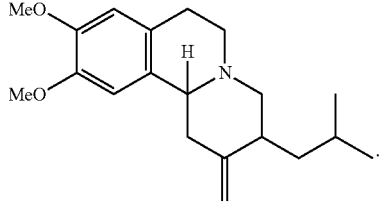

8. The method of claim 2, wherein the Aza-Prins cyclization reaction is performed in the presence of an oxidant selected from phenyliodine diacetate (PIDA), phenyliodine bis(trifluoroacetate)diacetate (FIFA) and dichlorodicyanoquinone (DDQ), a molecular sieve and LiClO$_4$.

* * * * *